Dec. 26, 1961 E. S. BOERNER Plant Pat. 2,114
ROSE PLANT
Filed Feb. 7, 1961
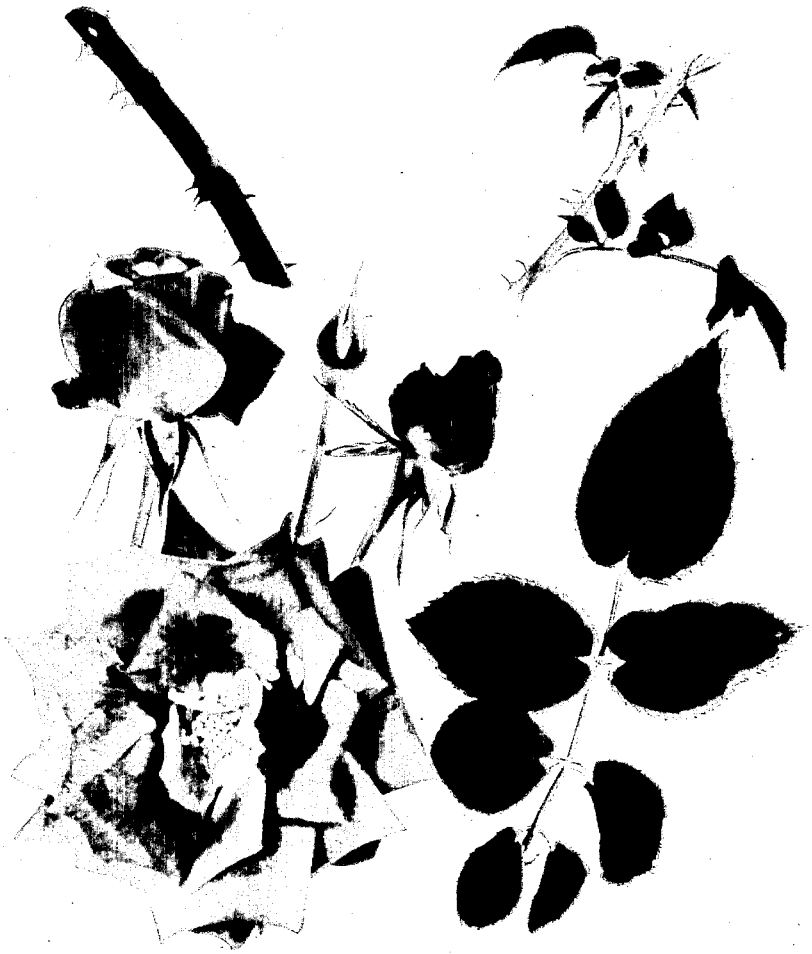
Inventor
E. S. Boerner
By: Robb & Robb
Attorneys United States Patent Office Plant Pat. 2,114
Patented Dec. 26, 1961

2,114
ROSE PLANT

Eugene S. Boerner, Newark, N.Y., assignor, by mesne assignments, to Home Nursery Products Corporation, Newark, N.Y., a corporation of New York Filed Feb. 7, 1961, Ser. No. 87,726
1 Claim. (Cl. 47—61)

The present invention relates to a new and distinct variety of rose plant of the hybrid tea class, which was originated by me by crossing an unnamed and unpatented seedling derived from a cross of "Poinsettia" (unpatented) × "Tawny Gold" (Plant Patent No. 950) with the variety "Detroiter" (Plant Patent No. 1,219).

The primary objective of this breeding was to produce a new and improved hybrid tea rose variety which bears bright, clear-colored red flowers. This objective was fully achieved, along with other desirable improvements, as evidenced by the following unique combination of characteristics which are outstanding and which distinguish it from its parents, as well as from all other varieties of which I am aware:

(1) A free blooming habit;

(2) An attractive flower form;

(3) Retention of the flower form throughout the blooming stage;

(4) Long-lasting qualities of the flowers, both as cut flowers and on the plant; and (5) A distinctive bright and clear Spectrum Red general color tonality of the flowers, lightly overcast with Carmine, and with a white eye in the center when fully open.

Asexual reproduction of my new variety by budding, as performed at Newark, New York, and also at Pleasanton, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Ridgway's Color Standards and Nomenclature:

Parentage:

*Seed parent.*—An unnamed seedling derived from a cross of "Poinsettia" × "Tawny Gold."

*Pollen parent.*—"Detroiter."

Classification:

*Botanic.*—Hybrid tea.

*Commercial.*—Hybrid tea.

Propagation: Holds its distinguishing characteristics through succeeding propagations by budding.

*Flower*

(Observations made from specimens grown outdoors at Newark, New York, near mid-afternoon during the middle part of the month of August.)

Blooming Habit: Recurrent—continuous.

Bud:

*Size.*—Large.

*Form.*—Ovoid; is not affected by wet or hot weather.

*Color.*—When sepals first divide—Spinel Red, Plate 26. When petals begin to unfurl—Carmine, Plate 1, lightly overcast with Oxblood Red, Plate 1. When half-blown: inside of petals — Carmine, Plate 1, lightly overcast with Spectrum Red, Plate 1, on the outer edge of the petals; reverse of petals—Scarlet-Red, Plate 1, lightly overcast with Carmine, Plate 1.

*Sepals.*—Slightly branched; curl back when petals begin to unfurl. Color: inside—Courge Green, Plate 17, with lower half of sepal overcast with Eugenia Red, Plate 13; outside—Light Cress Green, Plate 31.

*Calyx.* — Color — Light Cress Green, Plate 31. Shape — pear. Size — small. Aspect — smooth. Odor when rubbed—none.

*Peduncle.* — Length — medium. Aspect — rough. Strength — erect; heavy. Color — Light Cress Green, Plate 31, lightly overcast with Vinaceous Russet, Plate 28.

*Opening.*—Opens up well; is not affected by adverse weather conditions.

Bloom:

*Size.*—Large. Average size when fully expanded—from 3½ inches to 4 inches.

*Borne.*—Both singly and several together.

*Stems.*—Long; strong.

*Form (when first open).*—Cupped. Permanence—retains its form to the end.

*Petalage.*—Double (full but open center). Number of petals under normal conditions—from 50 to 55.

*Color.*—Center of flower—Carmine, Plate 1, with outer edge of petals lightly overcast with Spectrum Red, Plate 1, and with the lower part of the petals toward the base being White, Plate 53. Outer petals—Carmine, Plate 1. Base of petals (aiglet)—Barium Yellow, Plate 16. Inside of petals—Spectrum Red, Plate 1, lightly overcast with Carmine, Plate 1. Reverse of petals—Nopal Red, Plate 1, lightly overcast with Scarlet Red, Plate 1. General tonality from a distance—Spectrum Red, Plate 1, lightly overcast with Carmine, Plate 1.

*Discoloration.*—General tonality at end of first day—Carmine, Plate 1, lightly overcast with Spectrum Red, Plate 1. Second day—Carmine, Plate 1, lightly overcast with Spectrum Red, Plate 1. Third day—Spectrum Red, Plate 1, lightly overcast with Carmine, Plate 1.

Petals:

*Texture.*—Leathery; is not affected by wet or hot weather.

*Appearance.*—Inside—velvety. Outside—satiny.

*Form.*—Oval.

*Arrangement.*—Imbricated (regularly arranged shingle-like). Petaloids in center—few; large.

*Persistence.*—Drop off cleanly.

*Fragrance.*—Moderate. Nature—tea (average hybrid tea scent).

*Lasting quality.* — On the plant — long. As cut flower—long.

*Genital organs*

Stamens, Anthers: Medium size; regularly arranged around styles; many. Color—Pinard Yellow, Plate 4.

Stamens, filaments (threads): Medium length. Color—Cameo Pink, Plate 26.

Pollen: Color—Baryta Yellow, Plate 4.

Styles: Loosely separated; uneven length; medium length; thin.

Stigmas: Color—Salmon Buff, Plate 14.

Ovaries: All enclosed in calyx.

Hips: None.

Seeds: None.

*Plant*

Form: Bush.

Growth: Vigorous; upright.

Foliage: Compound of 3–5 leaflets.

*Size.*—Large.

*Quantity.*—Normal.

*Color.*—New foliage: upper side—Victoria Lake, Plate 1; under side—Oxblood Red, Plate 1. Old foliage: upper side—Dark, Dull Yellow-Green, Plate 32; under side—Chromium Green, Plate 32.

*Shape.*—Oval pointed.

*Texture.* — Upper side — leathery. Under side — smooth.

*Ribs and veins.*—Ordinary.

*Edge.*—Serrated (saw toothed).

*Serration.*—Both double and single; small.

*Leaf stem.*—Color—Light Bice Green, Plate 17. Under side—smooth.

*Stipules.*—Medium length; bearded.

Wood:

*New wood.*—Color—Yellowish Oil Green, Plate 5. Bark—smooth.

*Old wood.* — Color — Varley's Green, Plate 18. Bark—smooth.

Thorns:

*Thorns.*—Quantity: on main stalks from base—ordinary; on laterals from stalk—ordinary. Form—narrow base; medium length; some straight and some hooked downward. Color (when young)—Eugenia Red, Plate 13. Position—irregular.

*Prickles.*—Quantity: on main stalks—none; on laterals—none.

*Short needles.*—Quantity: on main stalks—none; on laterals—none.

I claim:

A new and distinct variety of rose plant of the hybrid tea class, substantially as herein shown and described, characterized particularly as to novelty by the unique combination of a free blooming habit, an attractive flower form, retention of the flower form throughout the blooming stage, long lasting qualities of the flowers both as cut flowers and on the plant, and a distinctive general color tonality of the flowers corresponding to Spectrum Red, lightly overcast with Carmine and with a white eye in the center of the flower when fully open.

No references cited.